(12) United States Patent
Mitsuru

(10) Patent No.: US 7,048,697 B1
(45) Date of Patent: May 23, 2006

(54) BIOLOGICAL INFORMATION COLLECTING DEVICE COMPRISING CLOSED PNEUMATIC SOUND SENSOR

(75) Inventor: Takashima Mitsuru, Tokyo (JP)

(73) Assignee: M-I-Laboratories Corporation, Tokyo (JP)

( * ) Notice: Subject to any disclaimer, the term of this patent is extended or adjusted under 35 U.S.C. 154(b) by 0 days.

(21) Appl. No.: 10/018,676

(22) PCT Filed: Aug. 30, 2000

(86) PCT No.: PCT/JP00/05902

§ 371 (c)(1),
(2), (4) Date: Dec. 24, 2002

(87) PCT Pub. No.: WO01/37731

PCT Pub. Date: May 31, 2001

(30) Foreign Application Priority Data

Nov. 24, 1999 (JP) .............................. 1999-332842
Mar. 31, 2000 (JP) .............................. 2000-099587

(51) Int. Cl.
*A61B 5/103* (2006.01)

(52) U.S. Cl. .................... 600/587; 600/529; 600/595
(58) Field of Classification Search ............ 600/300, 600/301, 481, 484, 500, 508, 527–529, 534, 600/552, 587, 595; 128/897, 898; 381/150, 381/355, 360; 340/573.1, 665, 666; 5/1, 5/600, 630, 652, 654, 713
See application file for complete search history.

(56) References Cited

U.S. PATENT DOCUMENTS 4,657,026 A * 4/1987 Tagg .......................... 600/534
4,862,144 A * 8/1989 Tao .......................... 340/573.1
5,684,460 A * 11/1997 Scanlon .................... 340/573.1
5,853,005 A * 12/1998 Scanlon ....................... 600/459
5,964,720 A * 10/1999 Pelz ............................ 600/595
6,146,332 A * 11/2000 Pinsonneault et al. ...... 600/534
6,416,483 B1 * 7/2002 Halleck et al. ............. 600/561
6,485,441 B1 * 11/2002 Woodward .................. 600/595

FOREIGN PATENT DOCUMENTS

JP          05192315  A  *  8/1993
JP          06030914  A  *  2/1994
JP          10014889  A  *  1/1998

* cited by examiner

*Primary Examiner*—Charles Marmor
(74) *Attorney, Agent, or Firm*—Robert D. Katz; Cooper & Dunham LLP (57) ABSTRACT

Conventionally, when a biological information collecting device is used for measurement, an electrode is directly attached to a human body, accurate information cannot be collected and measurement through a lead wire is performed, for long time constraining the human body because of the lead wire. A device proposed to solve the problem comprises a capacitive sensor used for detecting a signal from the human body, and therefore the temperature characteristics are not good, bringing out a drawback that the signal varies in a low-frequency range. A biological information collecting device according to the invention comprises a closed pneumatic sound sensor having a gas-tight air bag made of soft rubber, plastic, or cloth or a cabinet made of metal, rubber, plastic, or wood. Biological information about the respiration, the cardiac rate (cardiac cycle), and the body movement due to, e.g. a cough or a snore is collected by a microphone of a pressure sensor to perform measurement without constraining the human body, thereby solving the problem of the conventional devices.

6 Claims, 6 Drawing Sheets

BIOLOGICAL INFORMATION COLLECTING DEVICE COMPRISING CLOSED PNEUMATIC SOUND SENSOR

TECHNICAL FIELD

This invention relates to a biomedical information collection apparatus which uses a closed air type sound sensor mounted on a closed cabinet having a variable internal volume to collect biomedical information such as a heart rate, a respiration rate and movements of the body including a cough and a snore.

BACKGROUND ART

As a conventional apparatus for collecting biomedical information such as a heart rate, a respiration rate and movements of the body, an apparatus wherein electrodes for detecting various kinds of information are attached to the human body and signals detected by the electrodes are transmitted to a measuring instrument over lead wires to collect biomedical information of the human body is used frequently.

In such a conventional apparatus as described above, since the electrodes for information detection are attached to the human body, they are liable to be displaced from their original positions during use, resulting in variation of the output signals thereof and the collection lead wires are liable to suffer from disconnection at crossing points of the electrodes or folds of bedclothes, and where commercial power supply is used, there is a danger that, if the collection lead wires should contact with the living organism, then the living organism may receive an electric shock. Further, a lead wire is very likely to act as an antenna and suffer from external electromagnetic wave noise. In this manner, the conventional apparatus has various subjects to be solved. Further, not only accurate information cannot be collected for a long period of time, but also the freedom of the human body is lost owing to electrode fixing instruments and lead wires such that the human body is restricted even from tossing and turning in bed.

As a countermeasure for solving the problems of conventional biomedical signal detection apparatus of the type described, an apparatus disclosed in the official gazette of Japanese Patent Laid-open No. Hei 10-14889 has been proposed.

This apparatus includes body movement measurement means for measuring an oscillation signal of a living organism based on a series connection electrostatic capacity of a first electrostatic capacity formed between a first electrode and the living organism and a second electrostatic capacity formed between a second electrode and the living organism, and body pressure measurement means for measuring a body pressure signal originating from the weight of the living organism by means of the first or second electrode and a third electrode, and further includes calculation means for calculating a characteristic amount of the living organism such as the body weight, a heart rate, a respiration rate, an active mass or a life condition based on outputs of the body movement measurement means and the body pressure measurement means without adhering a measurement electrode directly to the living organism.

However, the apparatus disclosed in the official gazette of Japanese Patent Laid-Open No. Hei 10-14889 uses an electrostatic capacity type sensor to detect an oscillation signal of a living organism and uses a pressure-sensitive element to detect a body pressure signal originating from the weight of the living organism.

Generally, the electrostatic capacity type sensor is not good in temperature characteristic and exhibits a variation of a signal in a low frequency region in the proximity of the direct current. Meanwhile, the pressure-sensitive sensor has a creep characteristic and so forth and is low in response speed. In short, the pressure-sensitive sensor is poor in measurement accuracy of the absolute pressure and cannot catch a dynamic high frequency signal. Although it is a possible idea to use a distortion resistive element as the pressure-sensitive sensor, the output signal of the distortion resistive element is greatly dependent on environment such as installation conditions or the temperature. As a result, conventional biomedical signal sensors have a subject to be solved in that they are subject to such a restriction that the user itself performs zero point adjustment or gain adjustment every time a measurement is started, or a protection apparatus for stabilizing the installation environment of the sensor is provided separately, or else the biomedical signal sensor is used only as an on/off switch.

As a method which makes up for the drawback described above, a method has been proposed wherein a flexible closed body such as an air bag is placed under a living organism and a pressure variation in the closed body by a movement of the living organism is measured by a pressure sensor or a microphone to collect biomedical information.

However, in order to use this method to collect biomedical information in full and over a wide range, the closed body must be laid over a wide area.

Further, it is necessary to keep the internal pressure of the closed body higher than the external air pressure and use the closed body in an expanded condition.

DISCLOSURE OF INVENTION

According to the present invention, the problems of the conventional apparatus are solved by realizing a biomedical information collection apparatus wherein a plurality of closed air type sound sensors each formed from a non-directional microphone or/and pressure sensor for detecting and converting an air pressure in each of closed cabinets having air-tightness and each having a variable internal volume into an electric signal are used and a spring member placed in each of the closed cabinets, and the air pressures when a plate-shaped member is placed on the closed air type sound sensors in a state wherein air remains therein and a human body is placed on the plate-shaped member directly or with bedclothes or the like interposed therebetween are detected by the non-directional microphones or/and pressure sensors, whereby biomedical information such as the breath, the heart rate (cardiac cycle), or body movements including a cough or a snore of the human body can be measured without damaging the freedom of the human body.

With the biomedical information collection apparatus of the present invention, since the plate-shaped member is placed on the plurality of closed air type sound sensors in each of which a spring member is placed, a biomedical signal can be measured accurately over the entire range of the living organism. Therefore, the biomedical information collection apparatus is most suitable for remote supervision of an in-patient in a hospital and so forth.

BEST MODE FOR CARRYING OUT THE INVENTION

FIG. 1 is a schematic view showing an embodiment of a closed air type sound sensor used in the present invention and using a closed cabinet having a variable internal volume.

Figure 1A:
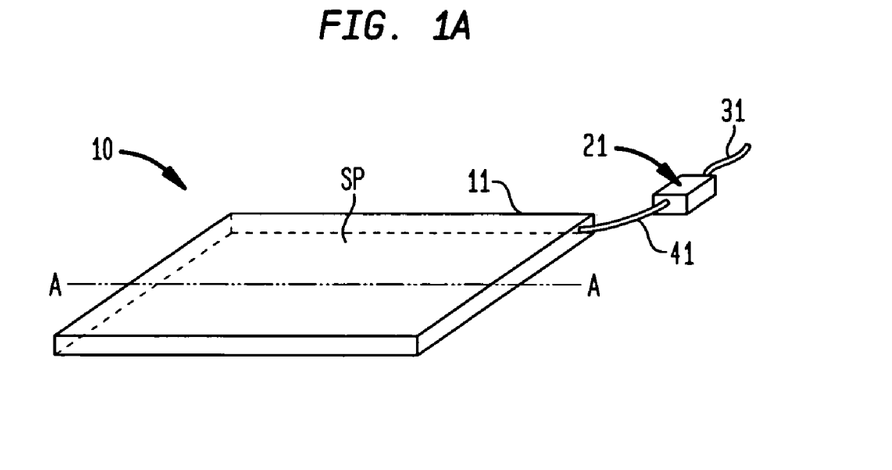
FIG. 1 is a schematic view showing an embodiment of a closed air type sound sensor used in the present invention and using a closed cabinet having a variable internal volume.
Figure 1B:
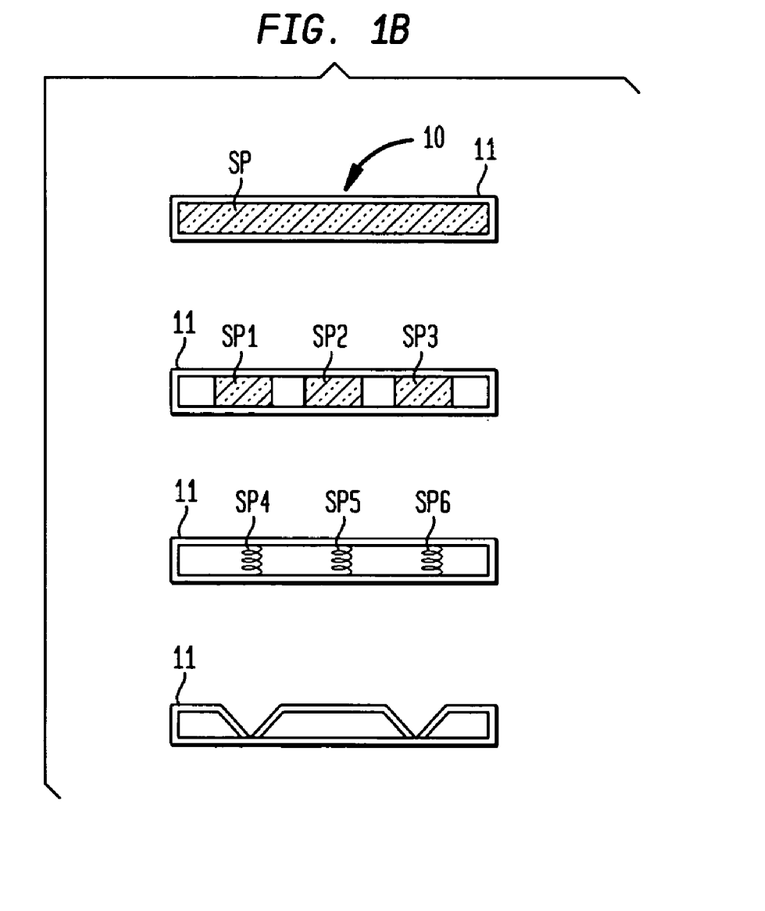

(a) of FIG. 1 is a schematic view showing a configuration of the closed cabinet having a variable internal volume, and (b) is a sectional view of the closed cabinet.

Referring to (a) and (b) of FIG. 1, reference numeral 11 denotes an airtight closed compartment, made of metal, rubber, plastics, wood or the like and having a variable internal volume. Reference character SP denotes a spring member for keeping an internal air gap of the closed compartment 11. Reference numeral 41 denotes an air pipe connected to the closed compartment 11. Reference numeral 21 denotes a non-directional microphone or pressure sensor, and 31 a lead wire for delivering a signal of the non-directional microphone or pressure sensor 21.

A state of arrangement of the spring member SP is described with reference to the sectional view of (b) of FIG. 1. (b) of FIG. 1 shows a cross section taken along plane A—A of (a) of FIG. 1, and (1), (2), (3) and (4) show examples which use spring members of different structures from one another.

(1) of (b) of FIG. 1 shows an example wherein the interior of the closed compartment 11 is filled with the spring member SP of continuous foamed sponge having an air permeability to support the air gap in the interior of the closed compartment 11. In this instance, the side walls of the closed compartment 11 are made of a flexible material so as to be movable when the shape of the spring member SP of the foamed sponge varies.

(2) of (b) of FIG. 1 shows an example wherein part of the interior of the closed compartment 11 is supported by independent foamed sponge elements SP1, SP2 and SP3 to support the air gap in the interior of the closed compartment 11.

(3) of (b) of FIG. 1 shows an example wherein a plurality of springs SP4, SP5 and SP6 are disposed in the interior of the closed compartment 11 to support the air gap in the interior of the closed compartment 11.

(4) of (b) of FIG. 1 shows an example wherein the closed compartment 11 itself is provided with resiliency by the shape of the surface material of the compartment to support the air gap in the interior of the closed compartment 11 and divide the interior of the closed compartment 11 into a plurality of air chambers.

Reference numeral 21 denotes a non-directional microphone or pressure sensor, and 31 denotes a lead wire for signaling a signal of the non-directional microphone or pressure sensor 21. Reference 41 denotes an air pipe connected to the closed compartment 11.

The non-directional microphone or pressure sensor 21 is attached to an end portion of the air pipe 41.

Air is enclosed in the interior of the closed compartment 11, and the pressure of the air is transmitted to the non-directional microphone or pressure sensor 21 through the air pipe 41. The non-directional microphone or pressure sensor 21 converts the internal pressure of the closed compartment 11 into an electric signal and transmits the electric signal over the lead wire 31.

The closed compartment 11 has a microscopic pinhole provided therein as an air leak countermeasure for minimizing the influence upon the non-directional microphone or pressure 21 which detects and converts the air pressure into an electric signal.

Figure 2:
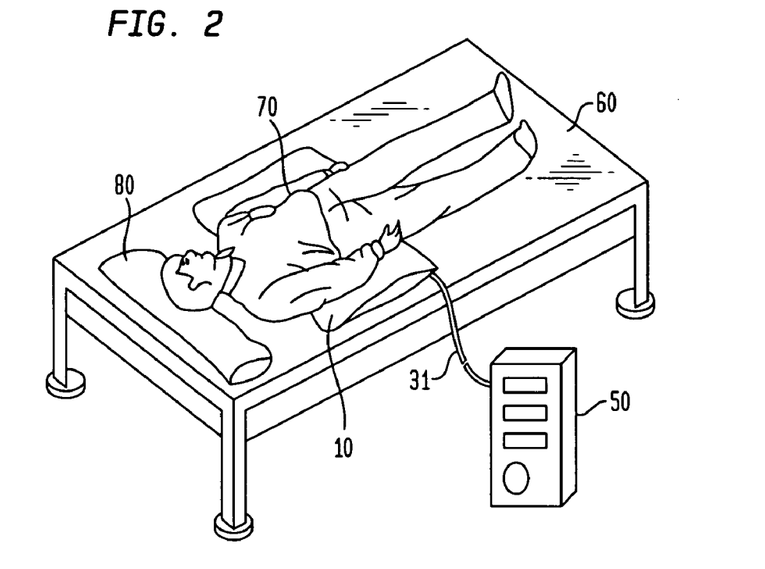
FIG. 2 is a view showing a conventional biomedical information correction apparatus which uses a pressure sensor.

FIG. 2 is a view showing a state of using a conventional biomedical information collection apparatus which uses a closed air type sound sensor.

Referring to FIG. 2, reference numeral 60 denotes a bed to be used by a person from whom biomedical information is to be collected. Reference numeral 50 denotes an information processing apparatus for collecting and processing biomedical information. Reference numeral 10 denotes a known closed air type sound sensor made of flexible rubber, plastic, cloth or the like. Reference numeral 31 denotes a lead wire for transmitting a detection signal of the closed air type sound sensor. Reference numeral 71 denotes a person from whom biomedical information is to be collected, and 80 a pillow to be used by the person from whom biomedical information is to be collected.

When it is intended to collect biomedical information such as a heart rate and a respiration rate of an in-patient in a hospital or the like for remote supervision, since it is necessary to perform a measurement for a long period of time, the measurement is performed while the person 71 whose biomedical information is to be collected is in a state wherein the person 71 lies on the bed 60 using the pillow 80. In this instance, the closed air type sound sensor 10 for collecting biomedical information is placed at a position of the back on which the weight of the closed air type sound sensor 10 whose biomedical information is to be collected is applied most, and the person 71 whose biomedical information is to be collected assumes a state where it lies on the closed air type sound sensor 10.

Involuntary mechanical movements such as breath and pulsation of the heart of the person 71 whose biomedical information is to be collected and involuntary mechanical movements of unconscious movements of the body such as tossing and turning are transmitted through the air enclosed in the interior of the closed air type sound sensor 10 to the non-directional microphone or pressure sensor, by which they are converted into an electric signal.

The electric signal detected by the closed air type sound sensor 10 is transmitted to the information processing apparatus 50 over the lead wire 31, and processing and supervision of the biomedical information are performed by the information processing apparatus 50.

In this method, a signal of a portion of the human body that goes beyond the closed air type sound sensor cannot be extracted readily, and in order to prevent this, it is necessary to make the area of the closed air type sound sensor greater than the size of the human body.

Figure 3:
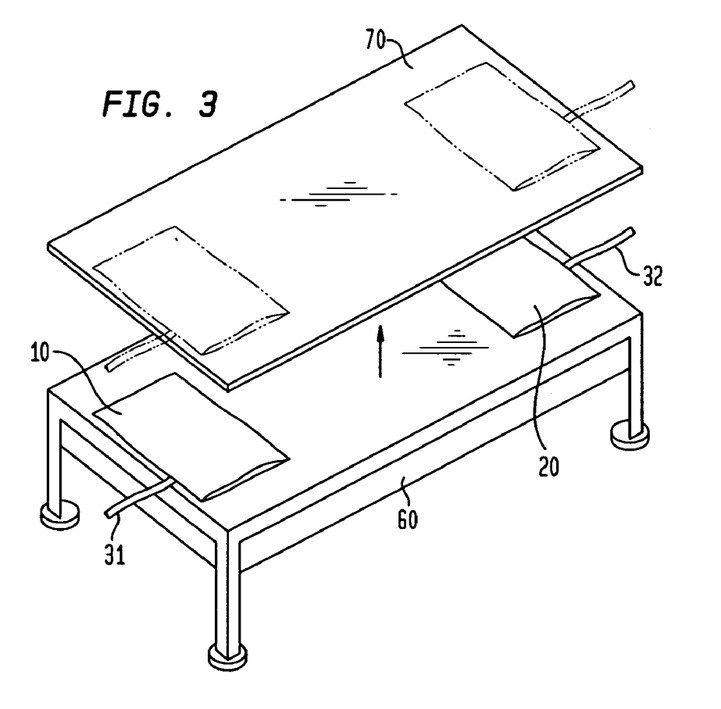
FIGS. 3 to 5 are views showing states of use of a biomedical information collection apparatus which uses the closed air type sound sensor of the present invention.

FIG. 3 is a view showing an embodiment of a biomedical information collection apparatus which uses the closed air type sound sensor of the present invention. Referring to FIG. 3, reference numeral 60 denotes a bed to be used by a person whose biomedical information is to be collected. Reference numerals 10 and 20 denote each a closed air type sound sensor having the configuration shown in FIGS. 1, and 31 and 32 denote lead wires for transmitting signals detected by the closed air type sound sensors. Reference numeral 70 denotes a plate-shaped member on which a person whose biomedical information is to be connected is to lie.

The closed air type sound sensors 10 and 20 are placed on the bed 60, and the plate-shaped member 70 is placed on them. The closed air type sound sensors 10 and 20 are placed at the opposite end portions of the plate-shaped member 70 and are set in such a positional relationship that the plate-shaped member 70 is supported by the closed air type sound sensors 10 and 20. In the case of the embodiment of FIG. 3, since a person whose biomedical information is to be collected lies on the closed air type sound sensors 10 and 20, even when the person whose biomedical information is to be collected in a state wherein the person lies on the plate-shaped member 70 changes the position of the body thereof by tossing and turning or the like, the biomedical information can be collected stably.

Figure 4:
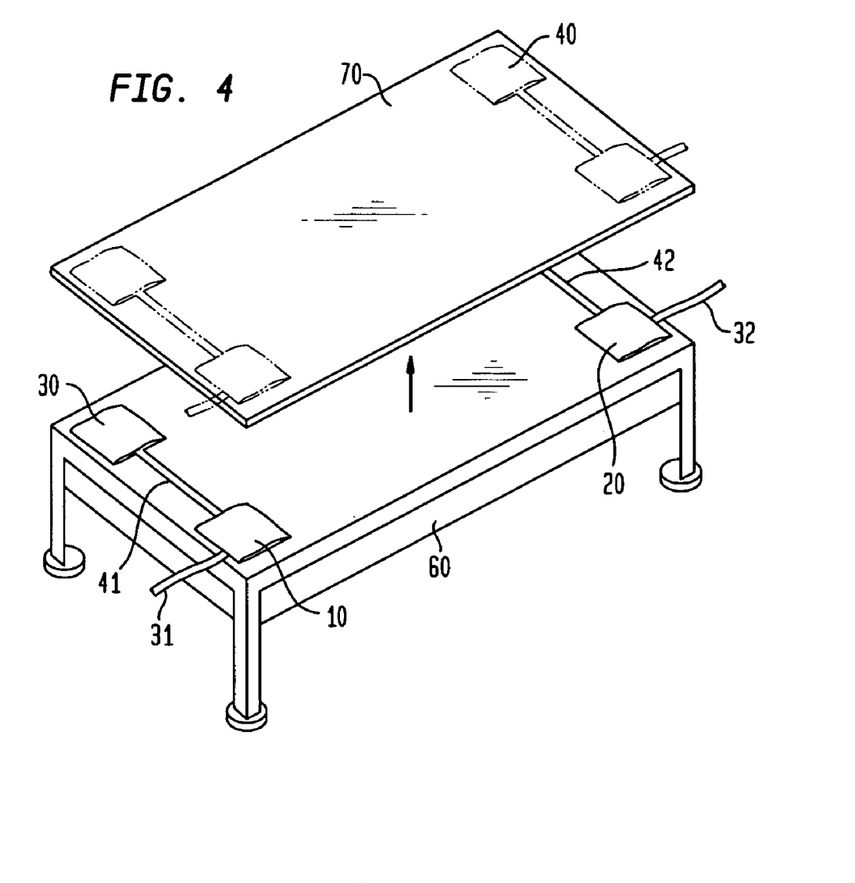

FIG. 4 is a view showing another embodiment of the biomedical information collection apparatus which uses the closed air type sound sensor of the present invention. Referring to FIG. 4, reference numeral 60 denotes a bed to be used by a person whose biomedical information is to be collected. Reference numerals 10, 20, 30 and 40 denote each a closed air type sound sensor having the configuration shown in FIG. 1. Reference numerals 31 and 32 denote lead wires for transmitting signals detected by the closed air type sound sensors, and 41 and 42 air pipes. Reference numeral 70 denotes a plate-shaped member on which a person whose biomedical information is to be collected is to lie.

The closed air type sound sensors 10, 20, 30 and 40 are placed at the four corners of the bed 60, and the plate-shaped member 70 is placed on them. The closed air type sound sensors 10, 20, 30 and 40 are placed at the four corners of the plate-shaped member 70 and set in such a positional relationship that the plate-shaped member 70 is supported by the closed air type sound sensors 10, 20, 30 and 40. In this instance, where closed air type sound sensors in each of which a sound sensor is provided in the interior of an air gap are used, if the air chambers of the closed air type sound sensors 10 and 30 and the air chambers of the closed air type sound sensors 20 and 40 are connected to each other by the air pipes 41 and 42, respectively, then it is possible to commonly use non-directional microphones or pressure sensors provided for the closed air type sound sensors 10 and 30 or 20 and 40 for detecting an air pressure. Also it is possible to interpose the closed air type sound sensors 10, 20, 30 and 40 in legs at the four corners of the bed 60.

Also where another closed air type sound sensor wherein a sound sensor is provided outside the air gap is used for the closed air type sound sensors 10, 20, 30 and 40, non-directional microphones or pressure sensors for detecting the air pressures of the air chambers of the closed air type sound sensors 10 and 30 or 20 and 40 can be used commonly.

In the case of the embodiment of FIG. 4, since a person whose biomedical information is to be collected lies on the closed air type sound sensors 10, 20, 30 and 40 with the plate-shaped member 70 interposed therebetween, even when the person whose biomedical information is to be collected in a state wherein it lies on the plate-shaped member 70 changes the position of the body by tossing and turning or the like, stable biomedical information can be collected at all times.

It is to be noted that, while, in the description of FIGS. 3 and 4, examples are described wherein a closed air type sound sensor is placed on the bed 60 and the plate-shaped member 70 is placed on the closed air type sound sensor, the closed air type sound sensor and the plate-shaped member 70 placed on the same need not necessarily be placed on the bed 60 but may be placed directly on a mat or the floor.

Figure 5:
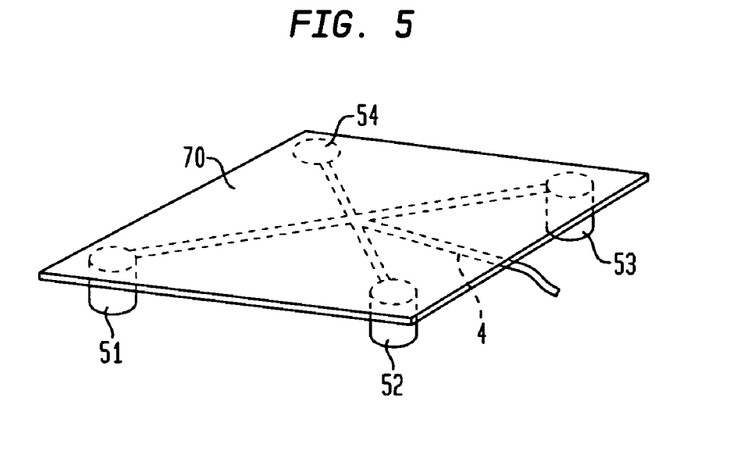

FIG. 5 is a view showing a further embodiment of a biomedical information collection apparatus which uses the closed air type sound sensor of the present invention. Referring to FIG. 5, reference numeral 70 denotes a plate-shaped member on which a person whose biomedical information is to be collected is to lie. Reference numerals 51, 52, 53 and 54 denote support posts for the plate-shaped member 70. Each of the support posts 51, 52, 53 and 54 is a closed air type sound sensor formed from a cabinet in which air is enclosed. In the air chamber of each of the support posts 51, 52, 53 and 54, a unique non-directional microphone or pressure sensor for detecting the air pressure of the air chamber can be provided. In this instance, an optimum one of signals of the sensors of the support posts can be selectively used. Also it is possible to connect the air chambers of the support posts 51, 52, 53 and 54 to one another by an air pipe 4 such that a single non-directional microphone or pressure sensor can be used commonly.

In the case of the embodiment of FIG. 5, since the closed air type sound sensors for collection of biomedical information support the plate-shaped member 70 at the four corners by means of the support posts each formed from a cabinet in which air is enclosed, also when the person whose biomedical information is to be collected in a state wherein it lies on the plate-shaped member 70 changes the position of the body by tossing and turning or the like, the biomedical information can be collected more stably.

The biomedical information collection apparatus which uses the closed air type sound sensor of the present invention is most suitable for remote supervision of an in-patient in a hospital or the like because it grasps the breath, the pulsation of the heart and body movements including a cough and a snore generally as a superimposed signal in a state wherein it does not restrict the behavior of the person lying on the plate-shaped member at all and can perform selection and analysis of the body movement times depending upon the amplitude and selection and analysis of the breach and pulsation of the heart depending upon the frequency.

The biomedical information detected by the closed air type sound sensor used in the biomedical information collection apparatus of the present invention includes involuntary mechanical movements such as the breath and the pulsation of the heart. The biomedical information further includes involuntary mechanical movements such as unconscious body movements such as tossing and turning, and during sleeping, also the unconscious body movements are significant information as a vigilance level.

In the remote supervision of an in-patient in a hospital or the like, it is possible to automatically detect from the state of biomedical information of the breath, respiration rate and so forth of the in-patient that the patient has fallen asleep and perform such an operation as to extinguish the light of the sickroom, switch off the television or adjust the sound volume of the radio set. Further, by incorporating the apparatus of the present invention into an article for daily use such as a bed, a chair, a carpet, a bathtub or a seat on a toilet bowl with which a living organism contacts, the condition of the health of the living organism can be discriminated without imparting an unfamiliar feeling to the living organism itself. It is known that an ordinary person who acts in the daytime exhibits the lowest temperature of a deep portion of the human body during sleeping around six o'clock in the morning, and essential biomedical information which is not influenced by the activity is obtained and can be coordinated with a cold or metabolism information such as a female periodic sexual hormone change.

Figure 6:
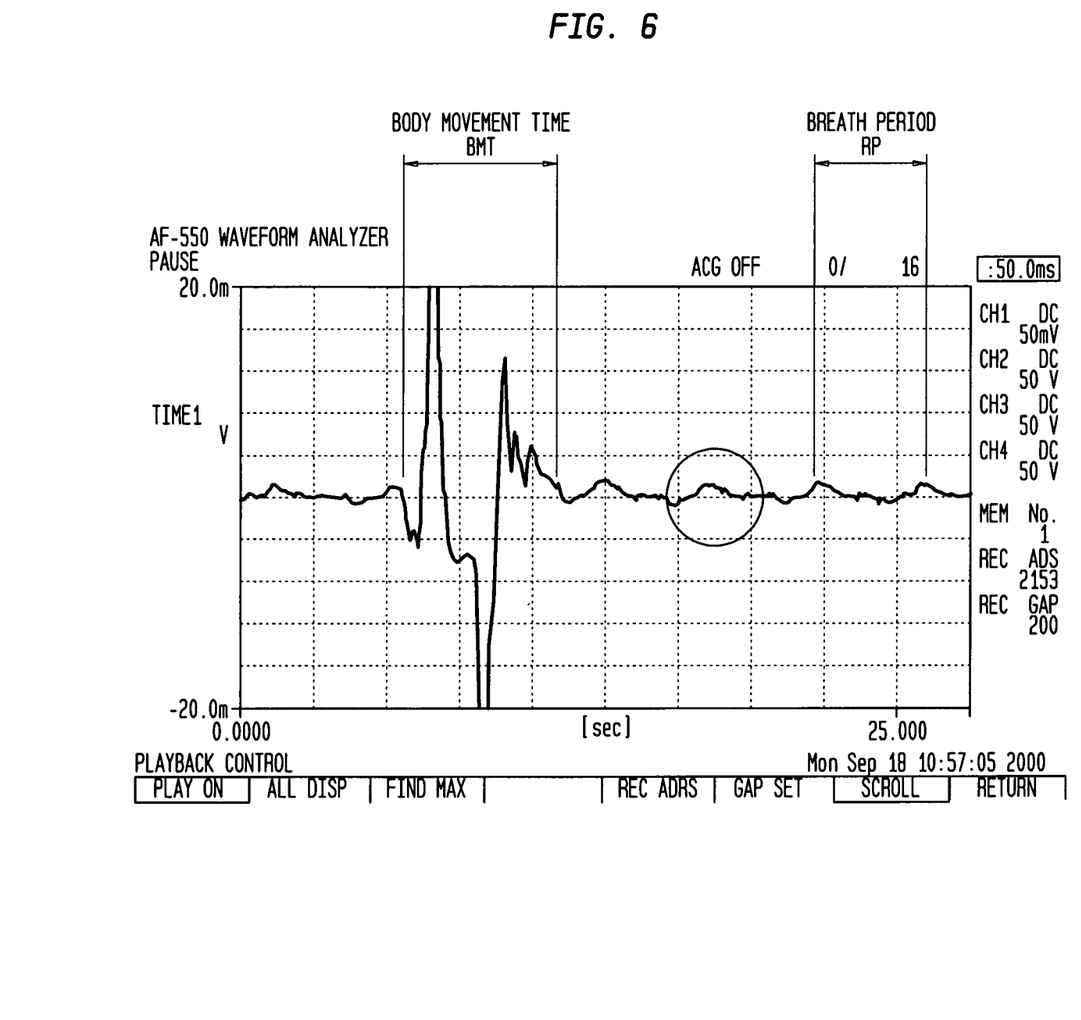
FIG. 6 shows an example of an output signal of a non-directional microphone of the enclosed air type sound sensor 10.

FIG. 6 shows an example of an output signal of the non-directional microphone of the closed air type sound sensor 10.

The axis of abscissa indicates the time (Sec), the axis of ordinate indicates the level (V) of the output signal. A portion of the output signal which exhibits a great variation in FIG. 6 indicates an involuntary mechanical movement BMT of unconscious body movements such as turning of the person 71 whose biomedical information is to be collected. Meanwhile, another portion of the output signal which exhibits a stable level and exhibits small variations indicates an involuntary mechanical movement such as breath or pulsation of the heart of the person 71 whose biomedical information is to be collected.

Figure 7:
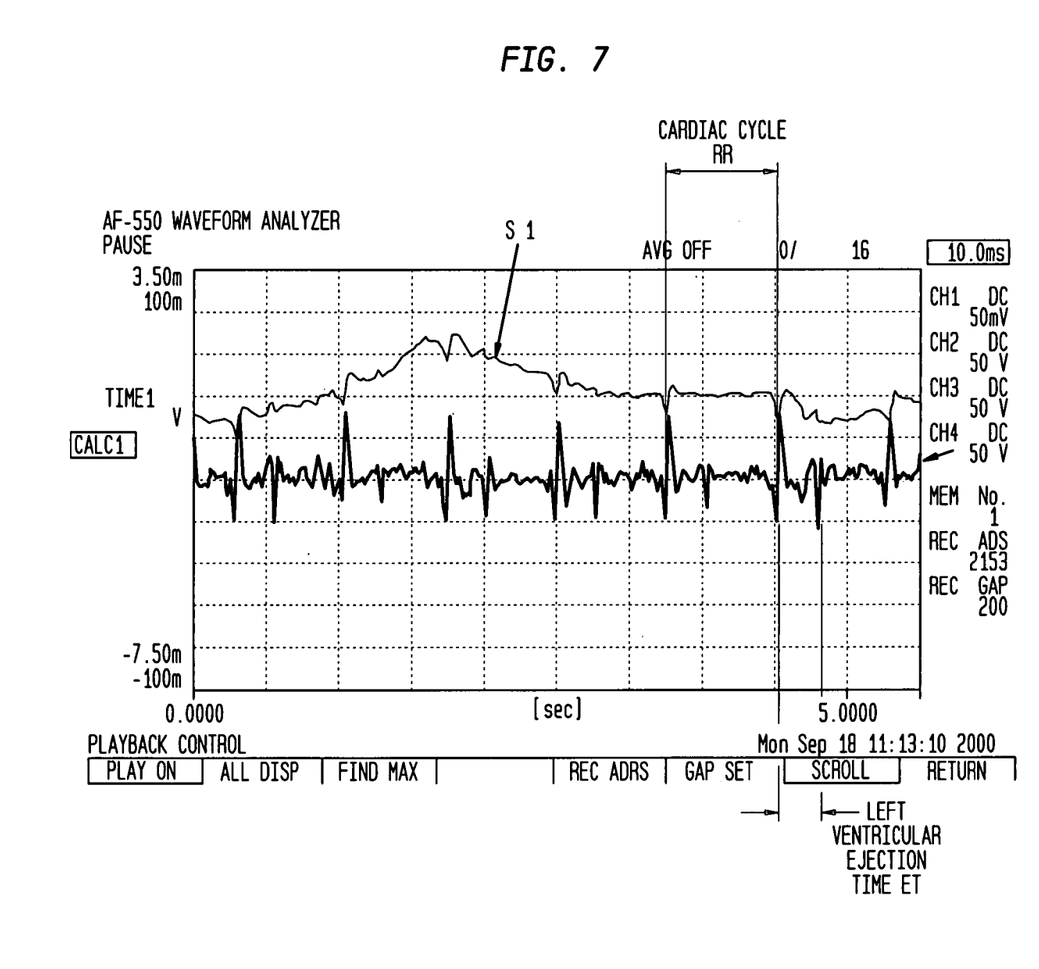
FIG. 7 shows a signal S1 obtained by enlarging a signal of a portion (portion surrounded by a circle in FIG. 6) whose level is stable but exhibits small variations from within the output signal of the non-directional microphone of the enclosed air type sound sensor 10 shown in FIG. 6 and another signal S2 obtained by differentiating the signal of the same portion.

FIG. 7 shows a signal S1 which is an enlarged signal of a portion of the output signal of the non-directional microphone of the closed air type sound sensor 10 shown in FIG. 6 within which the level is stable and exhibits small variations (portion surrounded by a circle in FIG. 6) and another signal S2 obtained by differentiating the signal at the portion.

A periodical signal in a high level of the waveform of the signal S2 obtained by differentiating the output signal of the non-directional microphone of the closed air type sound sensor 10 indicates a heart beat period, and the interval between a periodical signal of a high level and a periodical signal of an intermediate level indicates a left ventricular ejection time.

In this manner, various kinds of biomedical information can be obtained continuously over a long period of time from the output signal of the non-directional microphone of the closed air type sound sensor 10.

Figure 8:
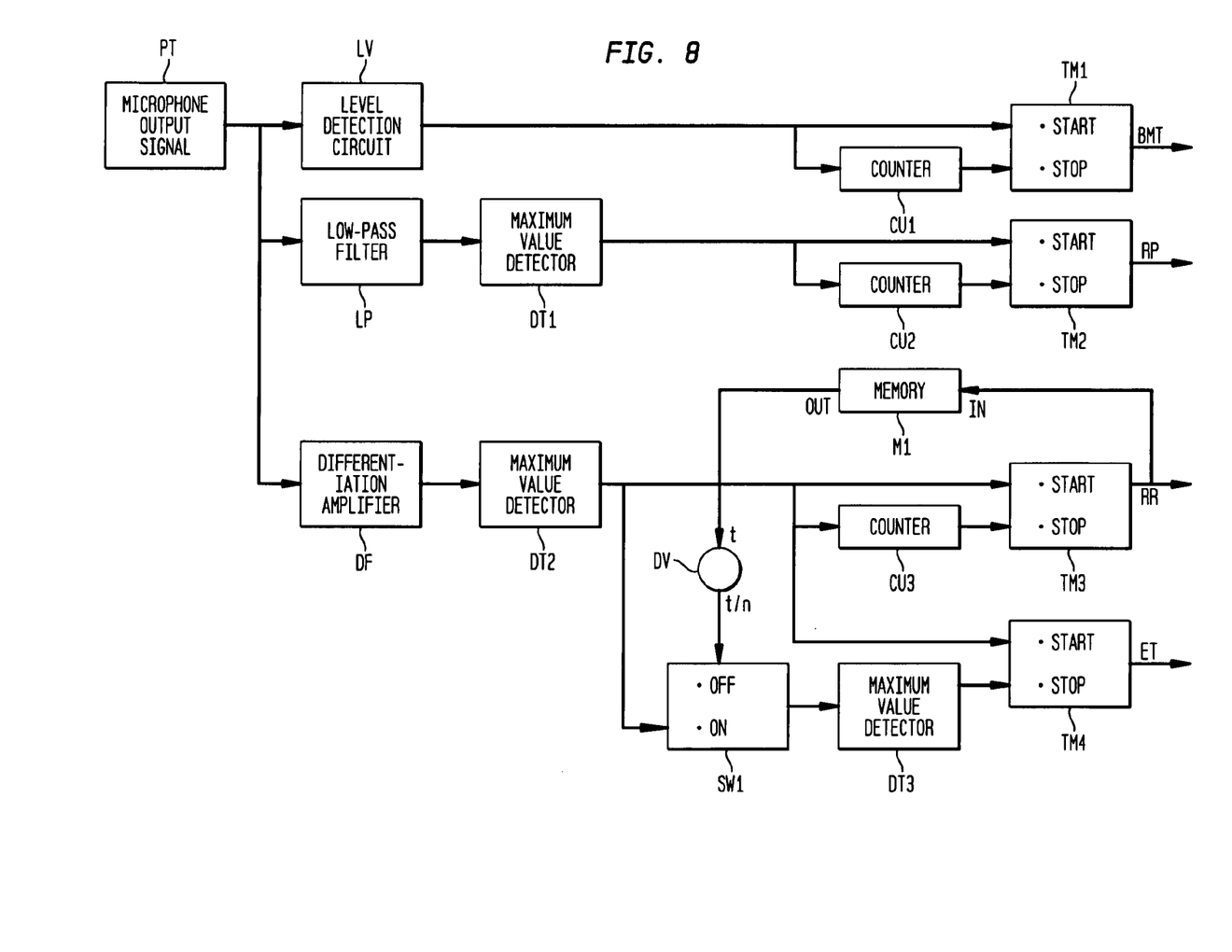
FIG. 8 is a block diagram showing an example of a signal processing circuit for processing the output signal of the closed air type sound sensor 10 to obtain various kinds of biomedical information.

FIG. 8 is a block diagram showing an example of a signal processing circuit for processing the output signal of the closed air type sound sensor 10 to obtain various kinds of biomedical information.

Referring to FIG. 8, reference character PT denotes the non-directional microphone of the closed air type sound sensor 10, which outputs such a signal as shown in FIG. 6.

Reference character LV denotes a level detection circuit, which outputs a pulse A when the output of the non-directional microphone PT exceeds a predetermined level. Reference character LP denotes a low-pass filter, which removes high frequency components of the output signal of the non-directional microphone PT. Reference character DF denotes a differential amplifier, which outputs such a signal as shown by S2 of FIG. 7 which is obtained by differentiating the output signal of the non-directional microphone PT.

Reference characters DT1, DT2 and DT3 denote maximum value detectors, each of which outputs a pulse of the positive polarity each time it detects a maximum value of a signal applied thereto.

Reference characters CU1, CU2 and CU3 denote counters, each of which counts pulses applied thereto and generates an output signal when the count value becomes equal to a preset value. Reference characters TM1, TM2, TM3 and TM4 denote timers, each of which measures a period of time after a signal is applied to a start terminal thereof until a signal is applied to a stop terminal thereof and outputs a result of the measurement at an output terminal thereof. Reference character DV denotes an attenuator, which attenuates a signal t applied thereto and outputs the attenuated signal. Reference character SW1 denotes a switch, and M1 a memory.

An output signal of the non-directional microphone PT is applied to the level detection circuit LV, low-pass filter LP and differentiation amplifier DF.

A pulse outputted from the level detection circuit LV is supplied as a start signal to the timer TM1 and applied also to the counter CU1.

The counter CU1 outputs a pulse of a different polarity each time it receives the pulse A outputted from the level detection circuit LV and is a preset counter which operates such that it outputs a pulse of the negative polarity when it receives the first pulse from the level detection circuit LV and then outputs a pulse of the positive polarity when it receives the next pulse.

The timer TM1 measures a period of time after it receives a positive polarity pulse from the level detection circuit LV until it receives a positive polarity pulse from the counter CU1, and outputs the measurement value as a body movement time BMT.

The output of the low-pass filter LP is applied to the maximum value detector DT1, and a pulse outputted from DT1 is supplied as a start signal to the timer TM2 and is further applied to the counter Cu2.

The timer TM2 measures a period of time after it receives a positive polarity pulse A from the maximum value detector DT until it receives a positive polarity pulse F from the counter CU2, and outputs the measurement value as a breath period RP.

The output signal of the differentiation amplifier DF is connected to the maximum value detector DT2.

A pulse outputted from the maximum value detector DT2 is supplied as a start signal to the timer TM3 and is further applied to the counter CU3. The timer TM3 measures a period of time after it receives a positive polarity pulse from the maximum value detector DT2 until it receives a positive polarity pulse from the counter CU3, and outputs the measurement value as a cardiac cycle RR.

The timer TM4 starts in response to a pulse outputted from the maximum value detector DT2 and switches ON the switch SW1 only for a period of time equal to 1/n the cardiac cycle RR prior by one heart beat measured by the timer TM3 and stored so that only an aortic valve closing sound is detected by the maximum value detector DT3 and applied as a stop signal to the timer TM4. Then, the measurement value of the timer TM4 is outputted as a left ventricular ejection time ET.

Operation of the circuit of FIG. 8 having such a configuration as described above is such as follows.

Such an electric signal of biomedical information as shown in FIG. 6 or as indicated by SI in FIG. 7 is outputted from the non-directional microphone PT. This signal indicates such involuntary mechanical movements such as the breath and the pulsation of the heart of the person 71 whose biomedical information is to be collected.

The level detection circuit LV outputs a pulse A when the electric signal of the output of the non-directional microphone PT exceeds a predetermined level, that is, when some body movement occurs with the person 71 whose biomedical information is to be collected, outputs the pulse A and supplies to the timer TMI. In response to the pulse A, the timer TMI starts a measurement of the body movement time BMT.

The timer TMI measures the period of time after it receives the pulse A from the level detection circuit LV until it receives a pulse B from the counter CU1, that is, the body movement time BMT of the person 71 whose biomedical information is to be collected shown in FIG. 6, and outputs the measurement value.

High frequency components of the electric signal of the output of the non-directional microphone PT originating from body movements and so forth are removed by the low-pass filter LP, and a maximum value of the electric signal, that is, a body movement of the person 71 whose biomedical information is to be collected originating from the breath, is detected by the maximum value detector DTI and a pulse A is outputted from the same.

The timer TM2 measures the period of time after it receives the pulse A from the maximum value detector DT1 until it receives the pulse B from the counter CU2, that is, the breath period RP shown in FIG. 6, and outputs the measurement value.

The electric signal of the output of the non-directional microphone PT is differentiated by the differentiation amplifier DF so that it is converted into such a signal as indicated by S2 of FIG. 7, and a maximum value of the differentiation signal is detected by the maximum value detector DT2.

The timer TM3 measures the period of time after it receives the pulse A from the maximum value detector DT2 until it receives the pulse B from the counter Cu3, that is, the cardiac cycle RR shown in FIG. 7, and outputs the measurement value.

Further, the timer TM4 switches ON the switch SW1 only for a period of time equal to 1/n the cardiac cycle RR prior by one heart beat after it receives the pulse A from the maximum value detector DT2, and measures the period of time until it receives the pulse B from the maximum value detector DT3, that is, the left ventricular ejection time ET shown in FIG. 7, and outputs the measurement value.

Various kinds of biomedical information can be obtained by processing the output signal of the closed air type sound sensor 10 by means of the signal processing circuit in this manner.

INDUSTRIAL APPLICABILITY

The biomedical information collection apparatus of the present invention can be used for a long period of time for both of an elderly person or a serious case weakened in physical fitness and conversely a living organism who moves actively because it uses a plurality of closed air type sound sensors each having a spring member in the interior thereof and can collect biomedical information from the overall area of a plate-shaped member placed on the closed air type sound sensors.

If the biomedical information collection apparatus which uses the closed air type sound sensor of the present invention is used together with short or long distance communication means, it is useful also as a monitor for an in-patient of a hospital, a monitor for a patient under medical treatment at home or a monitor during sleeping of a healthy person and can be applied also for detection of apnea syndrome, arhythmia during sleep and so forth. Further, it can be used also for observation of a variation of the heart rate or the breath arising from a cold, a change in hormone or fever. Furthermore, it allows also determination of the depth of sleep (REM sleep, NONREM sleep) and can provide a good timing for wakeup as well.

The invention claimed is:

1. A biomedical information collection apparatus, comprising:
   (a) a plurality of closed compartments, spaced apart and made of an airtight flexible material, each of the closed compartments having a variable internal volume; a spring member placed inside of each of the closed compartments;
   (b) a plurality of air pressure sensors each including one or more of a non-directional microphone or a pressure sensor, the air pressure sensors in communication with respective closed compartments for detecting and converting air pressure in each of the closed compartments into an electric signal; and
   (c) a plate-shaped member placed on the plurality of closed compartments, such that when a living organism is placed on the plate-shaped member placed on the plurality of closed compartments while air remains in the closed compartments and in the air pressure sensors, the air pressure in the closed compartments is detected by the respective air the air pressure sensors to measure biomedical information including breath, heart rate, and body movements including a cough and a snore of the living organism;
   wherein a microscopic pinhole is provided in each of the closed compartments to establish an air leak countermeasure to minimize an influence upon the air pressure sensors.

2. The biomedical information collection apparatus according to claim 1, wherein the air pressure sensors are mounted inside of each respective closed compartment.

3. The biomedical information collection apparatus according to claim 2, wherein the plate member is rigid.

4. The biomedical information collection apparatus according to claim 1, wherein the air pressure sensors are mounted at an end portion of a hose connected to the closed compartments.

5. The biomedical information collection apparatus according to claim 4, wherein the plate member is rigid.

6. The biomedical information collection apparatus according to claim 1, wherein the plate member is rigid.

* * * * *